United States Patent [19]

Hutchison

[11] Patent Number: 4,901,728
[45] Date of Patent: Feb. 20, 1990

[54] PERSONAL GLUCOSE MONITOR

[75] Inventor: Donald P. Hutchison, Knox County, Tenn.

[73] Assignee: EOL, Inc., Oak Ridge, Tenn.

[21] Appl. No.: 345,662

[22] Filed: May 1, 1989

Related U.S. Application Data

[63] Continuation-in-part of Ser. No. 200,130, May 31, 1988, abandoned.

[51] Int. Cl.$^4$ ................................................. A61B 5/00
[52] U.S. Cl. ..................................... 128/633; 128/664; 356/368
[58] Field of Search ............... 128/632, 633, 634, 664, 128/665; 356/364, 366, 368

[56] References Cited

U.S. PATENT DOCUMENTS

| | | |
|---|---|---|
| 3,958,560 | 5/1976 | March . |
| 3,963,019 | 6/1976 | Quandt . |
| 4,014,321 | 3/1977 | March . |
| 4,169,676 | 10/1979 | Kaiser . |
| 4,350,163 | 9/1982 | Ford et al. . |
| 4,427,889 | 1/1984 | Muller . |
| 4,498,774 | 2/1985 | Yeung et al. ........................ 356/368 |
| 4,586,513 | 6/1986 | Hamaguri . |
| 4,655,225 | 4/1987 | Dahne et al. . |

Primary Examiner—Kyle L. Howell
Assistant Examiner—John C. Hanley
Attorney, Agent, or Firm—Pitts and Brittian

[57] ABSTRACT

A device for the non-invasive determination of blood glucose of a patient. This glucose monitor is based upon the effect of glucose in rotating polarized infra-red light. More specifically, two orthogonal and equal polarized states of infra-red light of minimal absorption are passed through a tissue containing blood, and an accurate determination of change in signal intensity is made due to the angle of rotation of these states. This rotation depends upon the glucose level. In order to compensate for absorption in the tissue, another two orthogonal and equal polarized states of infra-red light are used, with the wavelength being selected to maximize absorption. At least two embodiments of forming the polarized states are described: an electro-optic switching unit, such as a lithium tantalate crystal with appropriately applied orthogonal voltages; and an infra-red beam splitter using two light sources. The device can be applied to a patient, for example, to monitor glucose levels and provide signals to an insulin pump so as to be an artificial pancreas.

9 Claims, 5 Drawing Sheets

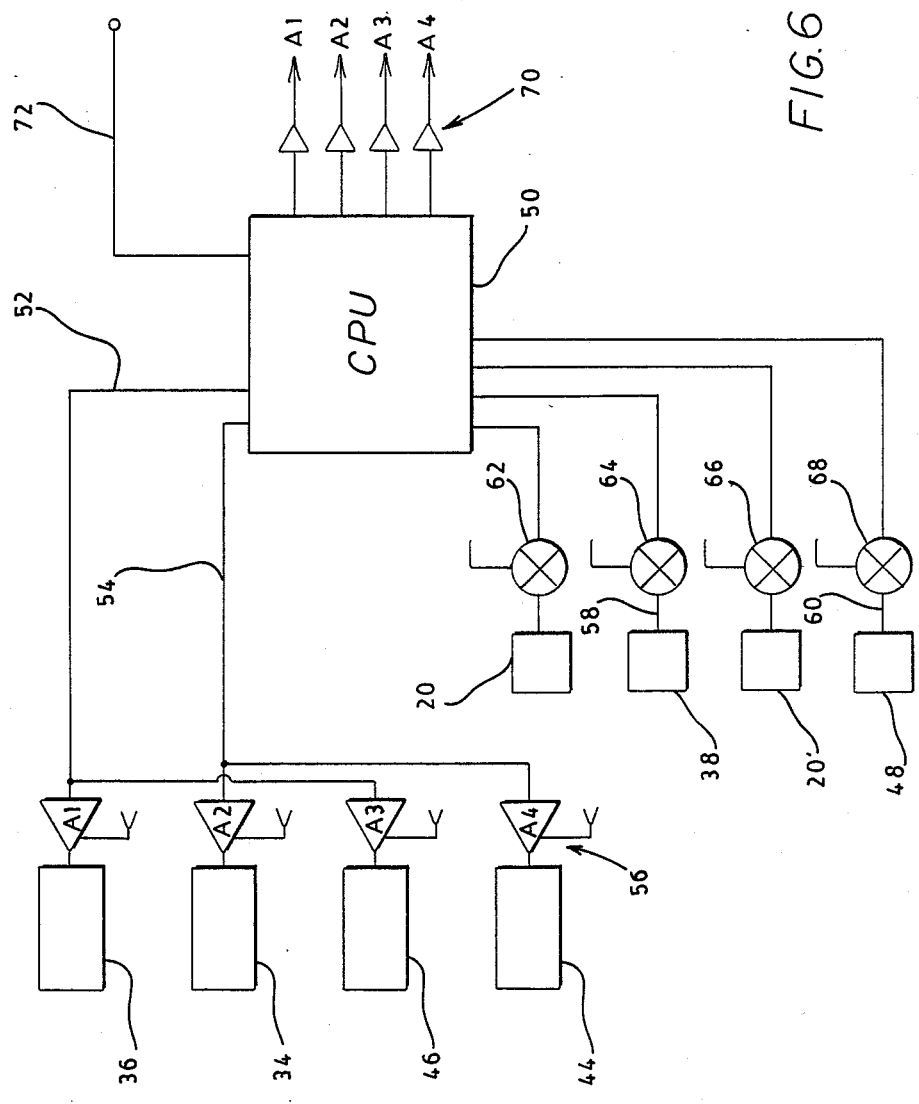

PERSONAL GLUCOSE MONITOR

This is a Continuation-in-Part application based upon parent application Ser. No. 200,130 filed May 31, 1988, now abandoned.

TECHNICAL FIELD

The present invention relates to an apparatus and a method for determining the level of glucose in a sample, and more particularly to a non-invasive personal glucose monitor for use by diabetics.

BACKGROUND ART

There are currently in excess of 10 million persons in the U.S. that are diabetics; i.e., exhibit an abnormal amount of blood glucose due to bodily misfunction. Many of these persons maintain control through periodic insulin injection, the amount and frequency of which are determined by testing for the blood glucose level. This testing can be in the form of periodic laboratory analysis, such as annual, semi-annual, or more frequent (e.g., daily) testing. The latter usually involves the drawing of blood through the pricking of the person's finger tip. The frequency of testing is dependent upon the sensitivity of the body to the insulin treatment. In severe cases an insulin pump is utilized for accomplishing frequent adjustment of the blood glucose level. Since the glucose level of an individual is not constant, a diabetic is usually given an amount of insulin based upon an average glucose level. Thus, there is a possibility that the patient can receive too little or too much insulin.

In order to reduce the pain of withdrawing blood, as well as potential infection, a non-invasive glucose determination would be desirable. Toward that end there have been certain devices developed for this purpose. For example, a device is described in R. S. Quandt U.S. Pat. No. 3,963,019, issued on June 15, 1976, that utilizes (in one embodiment) a beam of aqueous humor of the patient's eye. The level of glucose present affects the quantity of light exiting the eye, and this can be related to the glucose level. Another non-invasive glucose monitor which involves use of a patient's eye is described in W. F. March U.S. Pat. No. 4,014,321 (also 3,958,560), issued on Mar. 29, 1977. This device determines the optical rotation of polarized radiation as a function of the glucose level. Still other devices for determining the content of a patient's blood are described in N. Kaiser U.S. Pat. No. 4,169,676, issued Oct. 2, 1979; N. C. Ford, Jr. et al. U.S. Pat. No. 4,350,163, issued on Sept. 21, 1982; G. J. Muller U.S. Pat. No. 4,427,889, issued on Jan. 24, 1984; K. Hamaguri U.S. Pat. No. 4,586,513, issued on May 6, 1986; and C. Dahne, et al. U.S. Pat. No. 4,655,225, issued on Apr. 7, 1987. These devices depend upon absorption and/or backscattering of incident radiation to determine glucose levels.

The rotation of polarized radiation as a function of other organic molecules is reported in E. E. Yeung, et al. U.S. Pat. No. 4,498,774 issued on Feb. 12, 1985. The device thereof modulates a polarized laser beam using air gap Faraday rotators. While this device could have applications in the analysis of glucose in blood samples, it is hardly useful for non-invasive glucose analysis. As specified in Column 4 thereof, beginning at line 19, the device occupies a table about 4 feet×8 feet. Extreme care must be exercised to prevent vibration. The modulation as used in Yeung is very similar to that employed by one of the present inventors (Hutchinson) in a polarimeter described in "A Modulated Submillimeter-Laser Polarimeter for the Measurement of the Faraday Rotation of a Plasma", Appl. Phys. Letters, 34(3), page 218, Feb. 1, 1979.

Despite the developments made in this field of glucose analysis, none of the known devices have sufficient sensitivity to at all compare with the sensitivity achieved by more rigorous analytical techniques available in laboratories as applied to blood withdrawn from the body. Thus, none are suitable for controlling an insulin pump, for example. In the '321 patent referred to above, while it was previously known that glucose causes an optical rotation of polarized light (as used for sugar content in beers and the like), the degree of rotation caused by glucose levels of the body are extremely small and thus very difficult to measure with any sensitivity. A further drawback to certain of the prior art devices is that the patient's eye is used as the target. Considerable care would have to be exercised using these devices to prevent physical damage of some sort to the eye. Furthermore, insertion of any object in the eye is risky, and must be done carefully. These devices certainly cannot be used without professional help.

Accordingly, it is an object of the present invention to provide a non-invasive apparatus, and method for use of the apparatus, to determine glucose levels in the body with high sensitivity.

It is another object of the present invention to provide for the non-invasive detection of glucose levels without fear of physical damage to the patient.

An additional object of the present invention is to provide a non-invasive instrument for glucose determination that can be utilized by a lay person.

Another object of the present invention is to provide a non-invasive system; and its method of operation, that utilizes the optical rotation of two polarized and modulated orthogonal laser beams for increasing the sensitivity of glucose level detection in a patient.

A further object of the present invention is to provide non-invasive means for determining glucose levels in a patient with sufficient sensitivity such that output signals therefrom can be used to operate an insulin pump whereby the pump supplies only the amount necessary to maintain a desired glucose level.

These and other objects of the present invention will become apparent upon a consideration of the drawings hereinafter in combination with a complete description thereof.

DISCLOSURE OF THE INVENTION

In accordance with the present invention, there is provided a non-invasive personal glucose monitor having sufficient sensitivity to closely monitor glucose levels of a patient. This monitor includes means for producing a modulated polarized infra-red light beam having two orthogonal states, each having equal intensities and time duration but separated in time. In one preferred embodiment, the light has vertical polarization and horizontal polarization. This dually polarized light is passed through a tissue (sample) of the patient wherein the light is optically rotated in proportion to the glucose concentration. The transmitted light is then detected whereupon a rotational shift of both of the waves provides an increased signal differential to thereby significantly increase the sensitivity of the instrument. The preferred embodiments utilize light at two separate wavelengths to compensate for attenuation within the tissue.

BRIEF DESCRIPTION OF THE DRAWINGS

FIG. 6 is a block diagram of circuitry for or controlling the present invention.

BEST MODE FOR CARRYING OUT THE INVENTION

Figure 1:
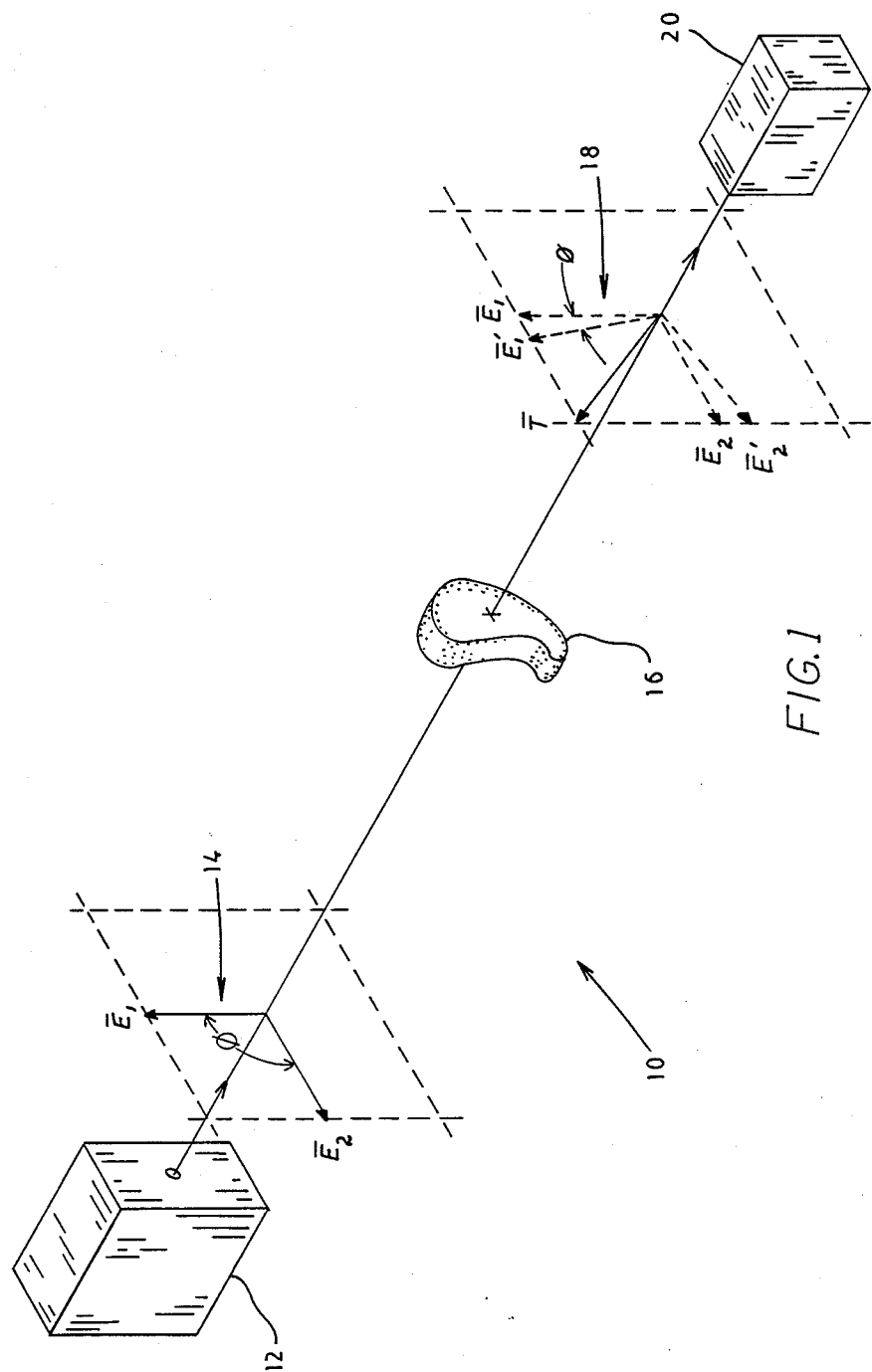
FIG. 1 is a schematic diagram of the present invention illustrating the major components thereof.

The principles of the present invention can be understood by reference to FIG. 1. Shown schematically at 10 therein is a personal glucose patient. The primary element of this monitor is a source 12 of linearly polarized, modulated infra-red light, the source being referred to hereinafter as a "polarization modulator means". This source is constructed to produce, as illustrated at 14, two light waves or states of different polarization and separated in time. These light waves, identified as $\overline{E}_1$ and $\overline{E}_2$, intentionally have the same intensity and are angularly separated by an angle, $\emptyset$, of ninety degrees. Thus, the two light waves are orthogonal. For convenience in a preferred embodiment, one of the waves is polarized vertically and the other is polarized horizontally. The duration, $\Delta t$, of these waves is selected to be equal, and this duration is typically 100 microseconds.

The modulated polarized light beam is then passed through a sample of tissue 16 having some level of glucose to be monitored. This tissue can be typically the ear lobe of a patient. As is known in the art, the glucose will cause an optical rotation to the polarized light. This is depicted at 18 where the angle of rotation, $\theta$, is directly proportional to the glucose level. A detector means 20 receives this optically-rotated light. Since the waves of light are discontinuous in separate time periods (see FIGS. 2A-B and 3A-B), circuitry (not shown) associated with the detector means measures the difference in the change in intensity of the light as the total shift caused by both waves; thereby, substantially increasing a signal produced by small values of $\theta$.

Figure 2A:
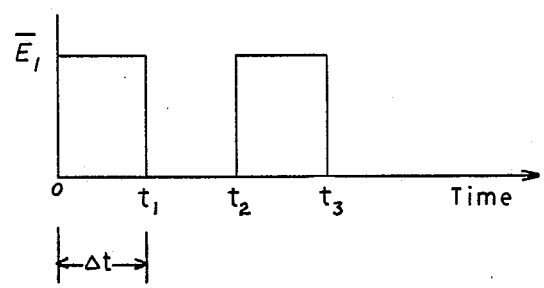
FIGS. 2A and 2B are waveforms of the individual waves from the modulated polarizer of FIG. 1.
Figure 2B:
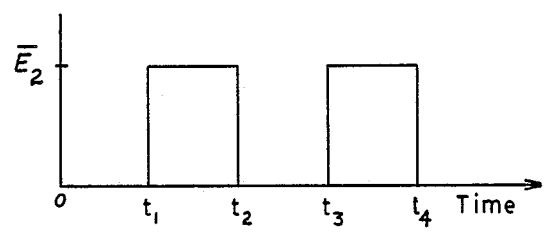

This can be better understood by reference to FIGS. 2A-B and 3A-B. The waveform of the two orthogonal light waves are shown in FIGS. 2A-B. It will be noted in FIGS. 2A-B that the two light wave intensities (of both $\overline{E}_1$ and $\overline{E}_2$) are equal, and each have the same duration, $\Delta t$, except they alternate in time, i.e., $E_1$, from 0 to $t_1$, and $E_2$ from $t_1$ to $t_2$.

Figure 3A:
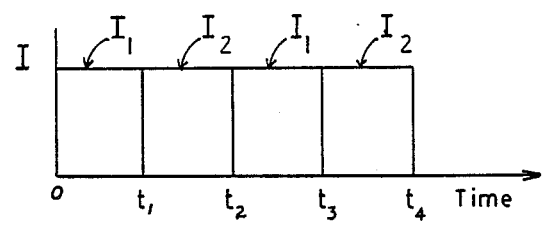
FIG. 3A is the waveform of the light at the detector of FIG. 1 when there is no rotation of the two polarized waves of light.
Figure 3B:
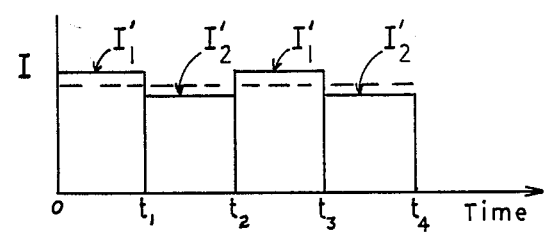
FIG. 3B is the waveform of the light at the detector of FIG. 1 when there is optical rotation of the two polarized waves of light as caused by blood glucose in the tissue.

Referring to FIG. 3A, shown therein signal intensity, I, at the detector 20 produced by the two waves if no optical rotation has occurred. As noted, the intensity $I_1$ for $\overline{E}_1$ is equal to the intensity, $I_2$, for $\overline{E}_2$. This could be the case of signals received with a zero glucose level or if the initial polarization orientation corresponds to the rotation that would occur with a selected glucose level as a standard. When optical rotation occurs, one of the two waves e.g., $\overline{E}_1$, will produce a larger signal strength $I_1'$ and the other wave a lower signal strength $I_2'$. This is illustrated in FIG. 3B. The detector means circuitry measures the difference between $I_1'$ and $I_2'$ and thus will distinguish the total shift which permits substantially increased sensitivity of measurement. Additional discussion of the increased sensitivity of the present invention will be given hereinafter with respect to FIG. 4A.

Figures 4, 4A:
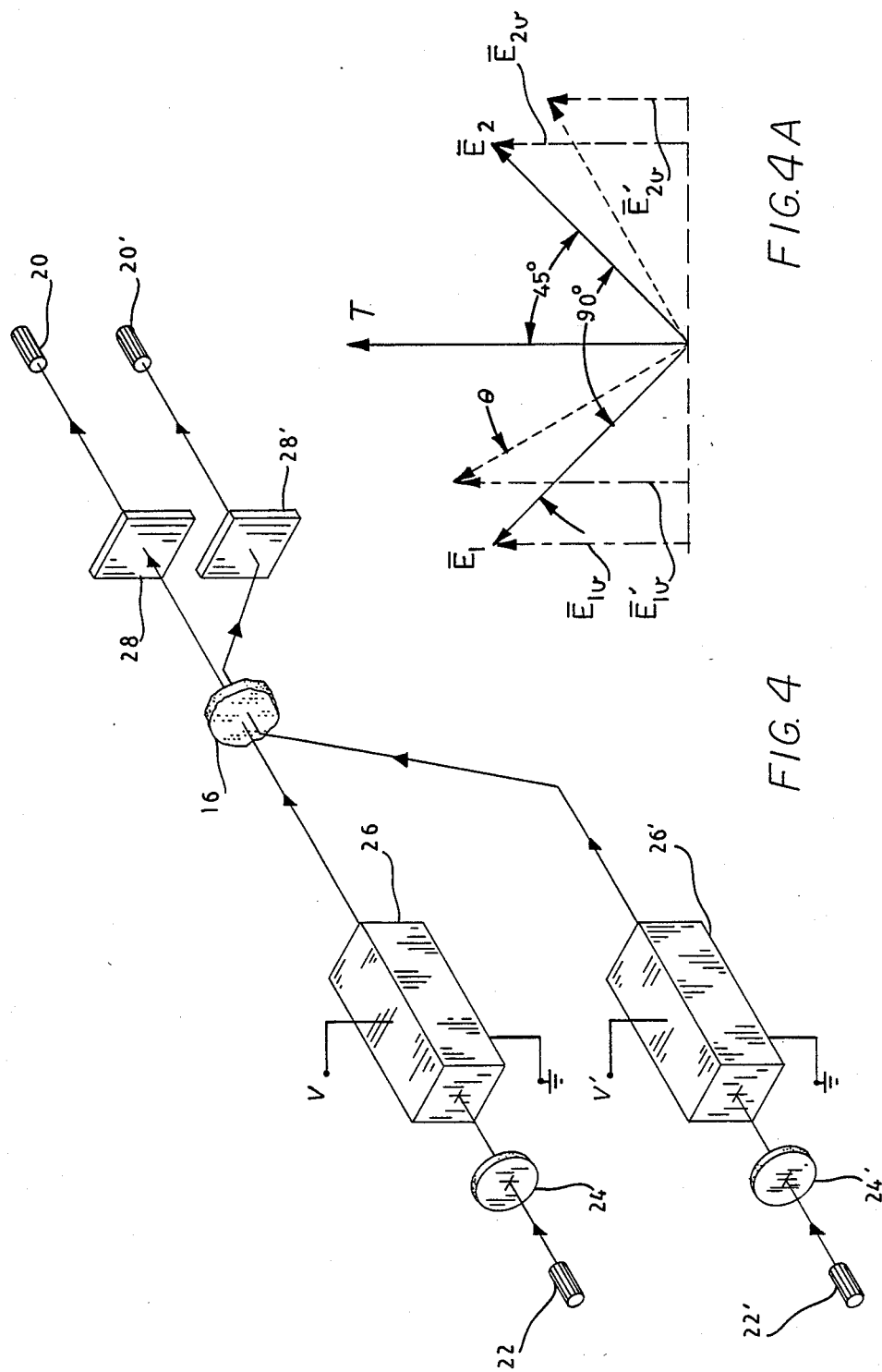
FIG. 4 is a schematic diagram of one embodiment of the present invention illustrating one means of achieving the modulated polarization as well as the dual components for use of two wavelengths to overcome attenuation in a tissue.
FIG. 4A is an illustration of the relationship between the two orthogonal phases of one of the wavelengths used in FIG. 4 showing their rotational position before and after passing through the tissue.

A schematic diagram of one specific embodiment of the present invention is depicted in FIG. 4. This embodiment utilizes a laser light source 22 producing light having a wavelength of, for example, 940 nm as produced typically with a NEC Model SE313 laser diode unit. While a wavelength of about 1000 nm is preferred for minimum absorption, apparatus for producing the 940 nm wavelength is available commercially. This light source is polarized in a linear direction. The light therefrom is passed through a conventional "quarter-wavelength" plate 24 that introduces a phase shift so as to change linear polarization to circular polarization. This shifted light is then passed through an electro-optic switching unit 26, such as a lithium tantalate crystal, again converting the polarization to linear but shifted ±45 degrees to the original linear polarization depending on the sign of the voltage, V, applied to the crystal. With an alternating square wave value of V, the shift will be back and forth as the potential switches. Thus, the equal waves $\overline{E}_1$ and $\overline{E}_2$ of FIG. 1 are produced such that each are orthogonal but still separated in time. In this embodiment, the quarter-wave plate 24 and the switching unit 26 make up the "polarization modulator means".

The waveforms of the light then are passed through the patient's tissue 16 which, as stated above, can be an ear lobe, a portion of the finger, or any other relatively thin portion of a patient. Glucose in this tissue causes the aforementioned rotation. The light is then shone through a polaroid material 28, this polaroid material having a transmission in a selected direction, i.e., in the same direction as the vertical component of each of the light states. This unit is referred to as a polarizer.

When no rotation has occurred, both waves or states produce a vector having equal vertical components. Thus, the signal transmission through the polarizer is equal for each of the vertical components such that the detector provides equal values of signals for the two waves. This is as depicted in the aforementioned FIG. 3A. If the values are substracted the result is zero. However, when rotation occurs due to glucose in the tissue, a new vector value is created for both waves, with the value of the vertical component of one vector increasing and the vertical component of the other decreasing. Thus, since the signals are substracted for even a very small angle of rotation, a greater distinction will be seen by the detector after the light passes through the polaroid material. This is as illustrated in FIG. 3B. The larger the rotation (due to glucose concentration) the larger will be the signal differences. If these signals are synchronously detected with a filter tuned to the switching frequency, there would be no signal for no sample, and an ever increasing signal for increasing glucose concentrations. Thus, even very small angles of rotation—a few thousands of a degree—produce a sufficiently changed electrical signal that can be processed using known amplification techniques.

This action of the polaroid material and rotation can be understood by referring to FIG. 4A. In this figure the two polarized light waves impinging upon a tissue are $\bar{E}_1$ and $\bar{E}_2$, just as indicated in FIG. 1. As before, they are orthogonal. Their particular orientation is selected relative to the transmission direction, T, of the polaroid material 28 such that each of the light waves has a vertical vector component $\bar{E}_{1v}$ and $\bar{E}_{2v}$ that will pass through the polaroid material to the detector means 20. When there is no rotation due to glucose, the values of $\bar{E}_{1v}$ and $\bar{E}_{2v}$ are equal and will cancel if subtracted (the detector is set to produce an output proportional to their difference). However, when rotation occurs, $\bar{E}_{1v}'$ becomes larger that $\bar{E}_{2v}'$. The sum and difference between these values achieves an output that provides information as to transmission and also is enhanced for a small angular rotation. This can be explained as follows. The "sum" voltage, $V_s$, signal at the detector means averaged over one cycle is $$<V_s> = kE^2[\cos^2(45° - \theta) + \cos^2(45° + \theta)]$$

$$\frac{<V_s>}{kE^2} = [\cos(45°)\cos\theta - \sin(45°)\sin\theta]^2 +$$

$$[\cos(45°)\cos\theta \, [-] \pm \sin(45°)\sin\theta]_2$$

Upon expanding, this becomes $$= 2\cos^2(45°)\cos^2\theta + 2\sin^2\theta.$$

Since $2 \cos^2(45°) = 2 \sin^2(45°) = 1$, and $\cos^2\theta + \sin^2\theta = 1$; therefore $$<V_s< = kE^2 \quad \text{(Equation 2)}$$

Therefore, the "sum" voltage signal averaged over one cycle is directly proportional to the signal transmitted through the sample. This "sum" signal depends only on transmission, not polarization rotation by the glucose in the sample.

The difference voltage signal, $V_d$, from the detector means 20 averaged over one cycle is $$<V_d> = kE^2[\cos^2(45° + \theta) - \cos^2(45° - \theta)] \quad \text{(Equation 3)}$$

$$\frac{<V_d>}{kE^2} = [\cos 45°\cos\theta - \sin 45°\sin\theta]^2 -$$

$$[\cos 45°\cos\theta - \sin 45°\sin\theta]^2$$

Upon expanding this becomes $$= 2 \sin 2\theta \quad \text{(Equation 4)}$$

Therefore, the magnitude of the difference signal averaged over one cycle is $$|V_d| = 2 kE^2 \sin 2\theta \quad \text{(Equation 5)}$$

For small values of $\theta$ $$|V_d| = 4kE^2\theta$$

Thus, the difference signal is directly proportional to the constant k times the transmitted signal times the angle of polarization rotation.

A portion of the problem of glucose monitoring in tissue, other than the very small amount of rotation due to the concentration of interest, is due to absorption in the tissue. This absorption is due to thickness, pigmentation, temperature, amount of blood, etc. This absorption can affect attenuation of the light seen by the detector. This can be overcome, however, by simultaneously making the measurements at two wavelengths whereby the attenuation of each (which depends on the absorption, see above) can be used to null the effect of absorption.

This manner of dealing with this problem is depicted in FIG. 4. A second light source 22' is used with a wavelength of, for example, 1300 nm. A source of this wavelength is commercially available and, with the 940 nm source, brackets the optimum wavelength of about 1000 nm. This 1300 nm wavelength typically is produced using an NEC Model ADL5340 laser diode. The linearly polarized light therefrom is passed through a quarter-wavelength plate 24' to produce circularly polarized light, and this passes into the switching unit 26', typically in the form of another lithium tantalate crystal. Through the application of potential V', applied as a square polarized and there will be two orthogonal waves separated in time according to the frequency of switching of V'. This light is passed through the tissue 16, through a second polarizer material 28' and is received by another detector means 20'.

It will be understood by persons versed in the art that light sources, power supplies and the like can have fluctuations. Accordingly, although not shown in FIG. 4, provision must be made for monitoring the light prior to impinging on the tissue 16 and for correcting for light intensity variation. Systems for affecting this type of "feedback" will be known to those skilled in the art. Furthermore, since the lithium tantalate crystals are sensitive to temperature change, means will be required to maintain the temperature of these crystals at a constant value.

Figure 5:
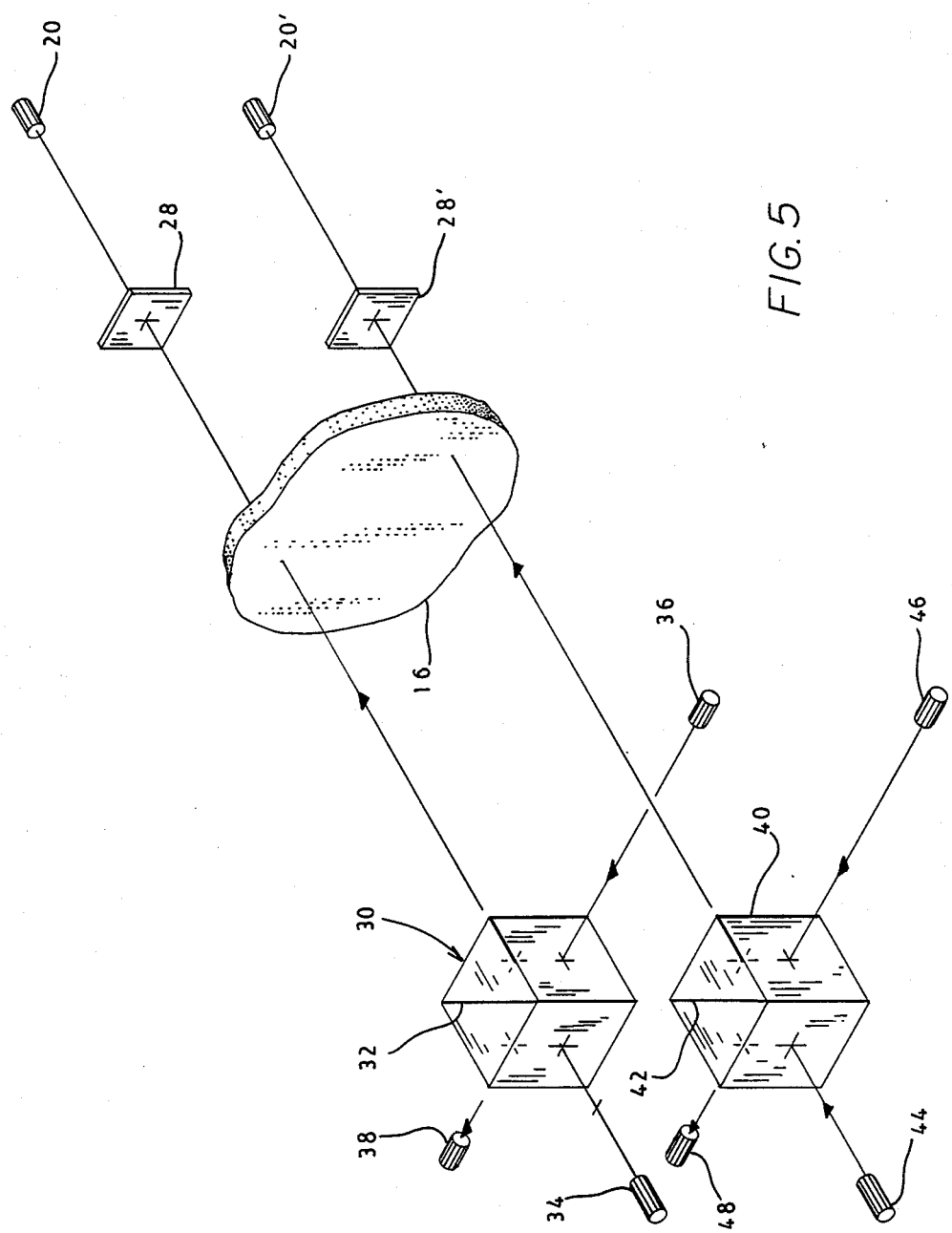
FIG. 5 is a schematic diagram of another embodiment of the present invention illustrating a further means of achieving the modulated polarization as applied to dual wavelengths.

Another embodiment of the present invention, although utilizing a different form of polarization modulator means, is illustrated schematically in FIG. 5. As with the embodiment of FIG. 4, light of two different wavelengths is used to negate the effect of absorption by the sample. In this embodiment, a first beam splitter means 30 is utilized for a first wavelength, e.g., 940 nm. This beam splitter means 30, typically NRC Model 05BC16, is essentially a cube of material (e.g., glass) that is transparent to the beam; in this instance, light at 940 nm. There is a diagonal plane 32 in the cube that is partially transparent to the light and partly reflective to that light. Two light-emitting diodes 34, 36, whose light is randomly polarized, are directed toward adjacent faces of the cube 30 so as to each be at a 45 degree angle to the plane 32. These light sources each can be, typically, an NEC SE313 LED. A unique result of this construction is that the transmitted light from light source 34 will be completely vertically polarized, and that from light source 36 will be completely horizontally polarized. Thus, through appropriate switching between the light sources 34 and 36, the two linearly polarized waves $\bar{E}_1$ and $\bar{E}_2$ are produced which are orthogonal (and separated in time) as in FIG. 1. The cube 30 can be physically oriented to produce these waves at +45 degrees and −45 degrees when desired (such as illustrated in FIG. 4A). Thus, with the same use of a polarizer material 28 and detector means 20, the rotation caused by glucose in the tissue 16 can be determined with precision (using the above equations). Since some of the light from each of the light sources is reflected by the diagonal plane 32, a single monitoring of this light with detector unit 38 permits a monitoring of the intensity of the light. Any conventional feedback circuit can be used to maintain equal intensities from sources 34, 36.

The second "channel" for this embodiment uses a second beam splitter 40 as the second polarization modulator means. This also has a partially reflecting diagonal plane 42. The same model of beam splitter is usable at the 1300 nm wavelength as used for the 940 nm. This wavelength is produced by each of the two light-emitting diodes (LED) 44, 46, such as NEC Model NDL-5310. As above, a detector 48 monitors the reflected portion of the light from plane 42 so as to provide a signal for feedback control. This second unit also provides two polarized waves such that absorption variations within the sample 16 can be negated. There is a second polarizer material 28' as well as a second detector means 20' for these measurements.

A typical implementation of an automatic control circuit for the glucose monitor system of FIG. 5 is illustrated in FIG. 6. The central portion of this circuit is a microprocessor/controller chip 50. This CPU chip is typically a NEC 78C10 unit. An oscillator within the CPU 50 provides two square waves 180 degrees out of phase on leads 52, 54 to drive both the 940 nm and 1300 nm wavelength emitters 34, 44, 36 and 46, respectively, in proper timing for the purpose discussed above through current sources shown at 56. The detectors 38, 48 provide signals on leads 58, 60 that are related to the light output of the 940 nm and 1300 nm emitters, respectively. Each of these detectors 38, 48 (as well as detectors 20, 20') utilize multiplier chips 62-68 between the detectors and the analog/digital (A/D) inputs of the CPU to allow phase-sensitive (synchronous) detection of the received signals. Typically these multiplier chips are National Semiconductor chips No. LH2228.

If the outputs from the emitters 34, 36, 44 and 46 change with time, the signals from the multipliers on each of the detectors 38, 48 will change. The CPU then adjusts the current to the appropriate emitter(s) to balance their light output. This current is provided through an appropriate one of several digital-to-analog converters (DAC) 70 as indicated.

As stated above, it is necessary for the measurement of optical rotation produced by the blood glucose level that the light intensities produced by the emitters 34 and 36 (and also emitters 44, 46) be equal. When any difference is noted, the CPU will adjust the drive currents through the appropriate DAC 70 to the appropriate current source 56. When the light intensities are balanced, the AC component of the signals appearing at the multipliers 62, 66 (from detectors 20, 20', respectively) will be directly proportional to the glucose level. The DC component of these signals is directly proportional to the attenuation of the 940 nm and 1300 nm light by the tissue. Using the two wavelengths, as explained above, permits the determination of tissue thickness from the attenuation information. This information, when combined with the rotation signals at the two wavelengths, can thus be used (with the equations set forth above) to accurately calculate the blood glucose level. The CPU 50 is preprogrammed to accomplish these calculations. A signal corresponding to this blood glucose level appears at output lead 72. This signal provides a potential readout of the glucose level and/or can be used to control an insulin pump.

From the foregoing, it can be seen that at least two embodiments of the present invention are presented. In both, there is a source of polarized infra-red light that is repetitively switched between two orthogonal linear polarization states of equal amplitude. It is this switching of the light, when passing through a tissue that increases the sensitivity of glucose detection. In order to negate absorption attenuation by the tissue, a second channel is used at a slightly different wavelength that closely brackets the optimum wavelength for minimal absorption by the tissue. Thus, although only specific embodiments have been described, the invention is not to be limited by these embodiments and the specific components referred to herein. Rather, the invention is to be limited only by the appended claims and their equivalents when taken together with the complete description of the invention.

I claim:

1. A device for the non-invasive determination of the concentration of blood glucose in a patient, which comprises:
   a first source of infra-red light of a selected wavelength;
   means for repetitively producing two alternating linearly-polarized orthogonal states of said infra-red light, said two states being equal in amplitude;
   means for directing said two states of said infra-red light through a selected tissue of said patient;
   polarizing means for receiving said two states subsequent to passage through said selected tissue of said patient;
   means for detecting the intensity of said polarized light of each of said states passing through said polarizing means; and
   means for determining a differential change in said intensity of said two states passing through said polarizing means as a result of rotation of said two states by glucose in said selected tissue of said patient to derive a signal related to concentration of said glucose.

2. The device of claim 1 wherein said infra-red light of said first source has a wavelength approximating a wavelength having minimal absorption in said selected tissue of said patient.

3. The device of claim 2 wherein said infra-red light has a wavelength of about 940 nanometers.

4. The device of claim 1 wherein said means for producing said two states comprises: means for producing said two states comprises:
   a quarter-wave plate for receiving said linearly polarized light to produce circularly polarized light; and
   an electro-optical switching crystal, having an alternating transverse voltage applied thereto, for receiving said circularly polarized light to repetitively and alternately form said two linearly polarized orthogonal states having equal intensities.

5. The device of claim 1 wherein said means for producing said two states comprises:

a cubical beam splitter having an internal diagonal semi-reflective plane oriented whereby said infra-red light from said first source impinges upon said plane at a 45 degree angle whereby light from said first source transmitted through said plane is linearly polarized in a first direction; and a further source of infra-red light of said selected wavelength directed at said beam splitter whereby light from said further source reflected by said plane in a same direction as said transmitted light from said first source is linearly polarized in a second direction orthogonal to said first direction.

6. The device of claim 5 further comprising a first detector to produce an output signal proportional to light of said first infra-red light source reflected by said plane:

a second detector to produce an output signal proportional to light of said further infra-red light source transmitted through said plane; and means for receiving said output signals of said first and second detectors and for adjusting current to said first and further infra-red light sources to maintain said two states equal in amplitude.

7. A device for the non-invasive determination of the concentration of blood glucose in a patient, which comprises:

a first source of infra-red light of a selected wavelength, means for repetitively producing two alternating linearly-polarized orthogonal states of said infra-red light, said two states being equal in amplitude, said means for producing said two states comprising a. a cubical beam splitter having an internal diagonal semi-reflective plane oriented whereby said infra-red light from said first source impinges upon said plane at a 45 degree angle whereby light from said first source transmitted through said plane is linearly polarized in a first direction, and b. a further source of infra-red light of said selected wavelength directed at said beam splitter whereby light from said further source reflected by said plane in a same direction as said transmitted light from said first source is linearly polarized in a second direction orthogonal to said first direction;

means for directing said two states of said infra-red light through a selected tissue of said patient;

polarizing means for receiving said two states subsequent to passage through said selected tissue of said patient;

means for detecting the intensity of said polarized light of each of said states passing through said polarizing means; and means for determining a differential change in said intensity of said two states passing through said polarizing means as a result of rotation of said two states by glucose in said selected tissue of said patient to derive a signal related to concentration of said glucose.

8. The device of claim 7 further comprising a first detector to produce an output signal proportional to light of said first infra-red light source reflected by said plane;

a second detector to produce an output signal proportional to light of said further infra-red light source transmitted through said plane; and means for receiving said output signals of said first and second detectors and for adjusting current to said first and further infra-red light sources to maintain said two states equal in amplitude.

9. The device of claim 7 wherein said infra-red light of said source has a wavelength approximating a wavelength having minimal absorption in said selected tissue of said patient.

* * * * *